United States Patent [19]

Hodgen

[11] Patent Number: 5,180,711
[45] Date of Patent: Jan. 19, 1993

[54] COMBINED TREATMENT WITH GNRH ANTAGONIST AND GNRH TO CONTROL GONADOTROPIN LEVELS IN MAMMALS

[75] Inventor: Gary D. Hodgen, Norfolk, Va.

[73] Assignee: Applied Research Systems ARS Holding N.V., Netherlands

[21] Appl. No.: 538,375

[22] Filed: Jun. 14, 1990

[51] Int. Cl.$^5$ .................... A61K 37/02; A61K 37/38; C07K 7/06
[52] U.S. Cl. ........................................ 514/15; 530/328
[58] Field of Search ........................... 514/15; 530/328

[56] References Cited

U.S. PATENT DOCUMENTS 4,845,077  7/1989  Hodgen ................................ 514/2

FOREIGN PATENT DOCUMENTS

WO89/01944  3/1989  World Int. Prop. O. .

OTHER PUBLICATIONS

Metrodin-The Gonadotropins in the Polycystic Ovarian Disease, product brochure of the Ares-Serono Group, 1990.
Coutts, Excerpta-Medica Int'l Congress Series 652:608 (1984).
Leal, Contraception 40:623, 1989.
Kenigsberg, J. Clin. Endocrinol. Metab. 62:734, 1986.
Chillik, Fertility and Sterility 48:480, 1987.

Primary Examiner—Lester L. Lee
Assistant Examiner—S. G. Marshall
Attorney, Agent, or Firm—Ostrolenk, Faber, Gerb & Soffen

[57] ABSTRACT

The present invention relates to a method of controlling gonadotropin levels in mammals which comprises administering a gonadotropin releasing hormone (GnRH) antagonist in an amount and frequency effective to substantially suppress endogenous gonadotropin levels in said mammal and administering gonadotropin releasing hormone (GnRH) in an amount and frequency effective to induce secretion of gonadotropins to maintain a desired level in said mammal. This method is especially useful for treating mammals, particularly women, who suffer from polycystic ovarian disease or hyperandrogenism, or who otherwise have abnormally high levels of luteinizing hormone which it is desired to reduce to approximately normal levels. The method of this invention is particularly advantageous for inducing ovulation in mammals, particularly women, that have the above-mentioned problems. The preferred GnRH antagonists for use in the present invention include Antide and its analogs, which exhibit long term gonadotropin suppression.

18 Claims, 1 Drawing Sheet

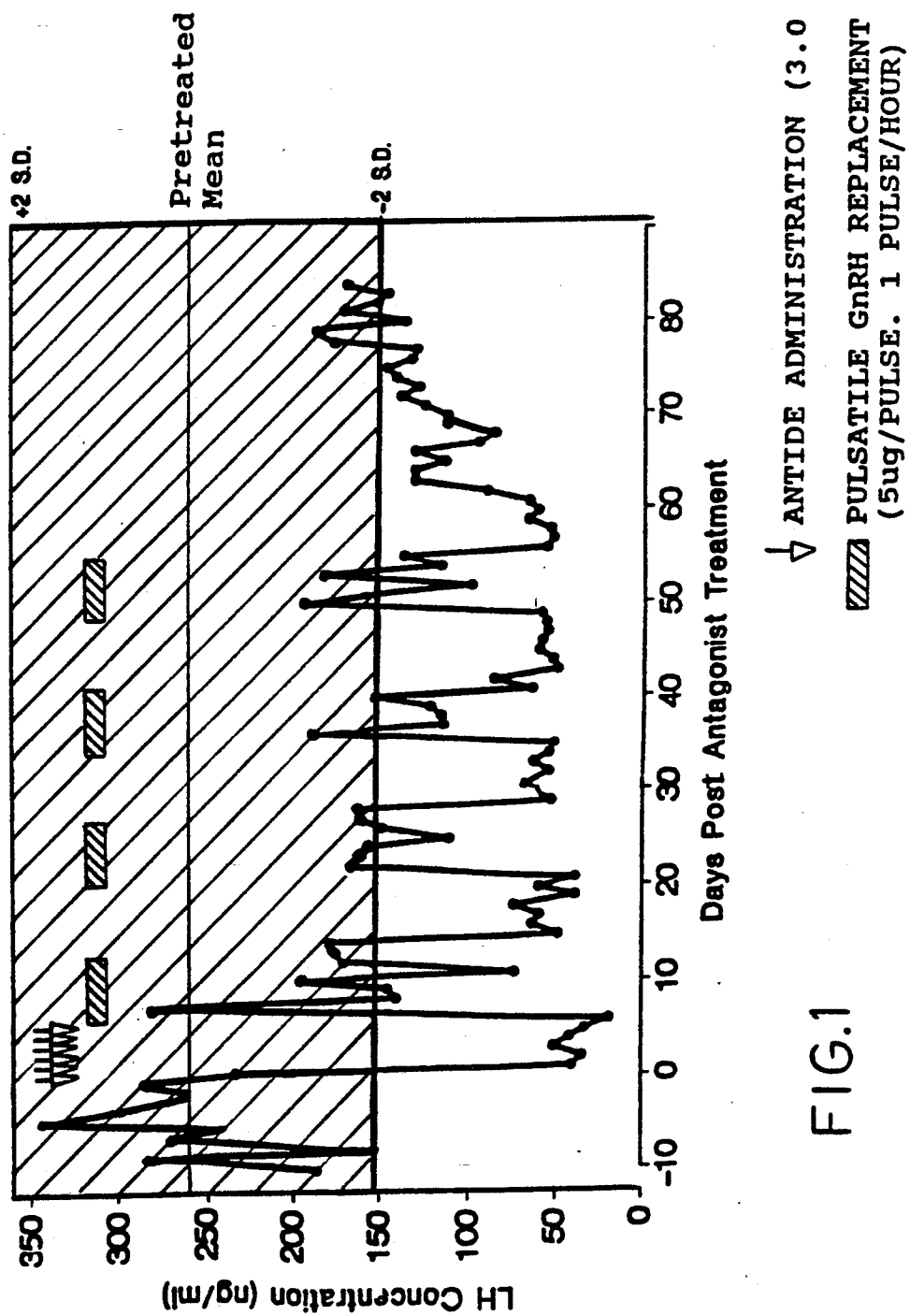

COMBINED TREATMENT WITH GNRH ANTAGONIST AND GNRH TO CONTROL GONADOTROPIN LEVELS IN MAMMALS

BACKGROUND OF THE INVENTION

A common problem encountered when treating female infertility is abnormal hormone levels, particularly, abnormally high luteinizing hormone (LH) and/or androgen levels, and often low follicle stimulating hormone (FSH) levels. This is especially true with patients suffering from polycystic ovarian disease (PCOD).

To induce ovulation and achieve a successful pregnancy in PCOD patients various treatments have been attempted. Excellent results have been obtained by administering essentially pure FSH, which has been found to correct the LH:FSH imbalance (METRODIN-The Gonadotropins in the Polycystic Ovarian Disease, product brochure of The Ares-Serono Group, 1990). It has also been suggested to administer a GnRH agonist (Hoe 766) to suppress endogenous gonadotropin (FSH/LH) secretion by a down-regulation mechanism and, while maintaining such suppression, administer a conventional gonadotropin treatment regimen to induce ovulation. (Coutts, Excerpta-Medica Int'l Congress Series 652:608, 1984). While not directed to treating PCOD, U.S. Pat. No. 4,845,077 suggests that the individual variability in response to gonadotropin therapy can be eliminated by cojointly administering a GnRH antagonist with the gonadotropin treatment.

A new generation of highly active GnRH antagonists are disclosed in WO 89/01944. While a large number of active decapeptides are disclosed in this publication, one of them has been tested more extensively than the others. This decapeptide has been named Antide and is represented by the formula N—Ac—D—2—Nal—D—pClPhe—D—3—Pal—Ser—NicLys—D—NicLys—Leu—ILys—Pro—D—Ala—$NH_2$. Antide has been shown to provide profound long-term inhibition of tonic gonadotropin (FSH/LH) levels in ovariectomized monkeys, the duration of such inhibition being dose dependent (Leal et al, J. Clin. Endocrinol. Metab. 67:1325, 1988). More recently, it was discovered that ovariectomized monkeys treated with Antide would respond to a large i.v. bolus of gonadotropin releasing hormone (GnRH) by showing a transient increase in gonadotropin levels which subsequently fell back to the inhibited state (Leal et al, Contraception 40:623, 1989).

SUMMARY OF THE INVENTION

The present invention relates to a method of controlling gonadotropin levels in mammals which comprises administering a gonadotropin releasing hormone (GnRH) antagonist in an amount and frequency effective to substantially suppress endogenous gonadotropin levels in said mammal and administering gonadotropin releasing hormone (GnRH) in an amount and frequency effective to induce secretion of gondotropins to maintain a desired level in said mammal. This method is especially useful for treating mammals, particularly women, who suffer from polycystic ovarian disease or hyperandrogenism, or who otherwise have abnormally high levels of luteinizing hormone which it is desired to reduce to approximately normal levels. The method of this invention is particularly advantageous for inducing ovulation in mammals, particularly women, that have the above-mentioned problems. The preferred GnRH antagonists for use in the present invention include Antide and its analogs, which exhibit long term gonadotropin suppression.

DESCRIPTION OF THE DRAWINGS

FIG. 1 is a graph which illustrates LH response levels in ovariectomized cynomolgus monkeys treated with Antide, followed by pulsatile GnRH replacement therapy in a 7 day on, 7 day off regimen.

DESCRIPTION OF THE PREFERRED EMBODIMENTS

In practicing the treatment method of the present invention, it is preferred to utilize a GnRH antagonist which exhibits a long inhibition of gonadotropin secretion. Particularly advantageous are the GnRH antagonists of the type disclosed in WO 89/01944, the disclosure of which is incorporated herein by reference. These GnRH antagonists include decapeptides which have the formula:

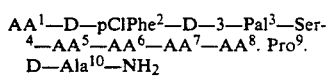

wherein $AA^1$ is N—Ac—D—2—Nal, N—Ac—D—pClPhe or N—Ac—D—$Cl_2$Phe;

$AA^5$ is Tyr, acylated Lys or D-acylated ACAla;
$AA^6$ is D-acylated Lys or D-acylated ACAla;
$AA^7$ is Leu, Aile, Nle, Val, NVal, Abu, or Ala; and
$AA^8$ is ILys or IOrn.

as well as structural analogs and derivatives thereof which have essentially the same activity. Such analogs and derivatives include, for example, those peptides wherein one or more amino acids have been modified, such as by substituting a different amino acid, and/or adding a substituent, such as alkyl, where such modification does not destroy the essential properties of the peptide.

Of the decapeptides which are embraced by the above-mentioned formula, especially preferred are those wherein $AA^1$ is N—Ac—D—2—Nal
$AA^2$ is NicLys, PicLys, MNicLys, MPicLys, INicLys, DMGLys, or PzcLys; and
$AA^6$ is D-NicLys, D-PicLys, DMNicLys, D-MPicLys, D-INicLys, D-BzLys, D-PzcLys, D-PzACAla, D-NACAla, or D-PACAla.

The most preferred GnRH antagonist is Antide, which is represented by the formula N—Ac—D—2—Nal—D—pClPhe—D—3—Pal—Ser—NicLys—D—NicLys—Leu—ILys—Pro—D—Ala—NH2. Of course, other known GnRH antagonists may also be utilized, including, for example, (N—Ac—D—2—$Nal^1$, D—$pClPhe^2$, D—3—$Pal^3$, $Arg^5$, D—$Glu^6$(AA), D—$Ala^{10}$)—GnRH and (Ac—$pClPhe^1$, $pCloPhe^2$, D—$Trp^3$, D—$Arg^6$, D—$Ala^{10}$)—GnRH.

In the above formulations, the following abbreviations apply:

| | |
|---|---|
| Ac = | acetyl |
| Abu = | aminobutyric acid |
| ACAla = | aminocyclohexylalanine |
| Aile = | alloisoleucine |
| Ala = | alanine |

| | -continued |
|---|---|
| BzLys = | $N^E$-benzoyllysine |
| Cl₂Phe = | 3,4-dichlorophenylalanine |
| DMGLys = | $N^E$-(N,N-dimethylglycyl) lysine |
| Ilys = | $N^E$-isopropyllysine |
| INicLys = | $N^E$-isonicotinoyllysine |
| IOrn = | $N^d$-isopropylornithine |
| Leu = | leucine |
| Lys = | lysine |
| MNicLys = | $N^E$-(6-methylnicotinoyl) lysine |
| MPicLYS = | $N^E$-(6-methylpicolinoyl) lysine |
| NACAla = | 3(4-nicotinoylaminocyclohexyl) alanine |
| 2-Nal = | 3-(2-naphthyl) alanine |
| NicLys = | $N^E$-nicotinoyllysine |
| Nle = | norleucine, 2-aminohexanoic acid |
| Nval = | norvaline, 2-aminopentanoic acid |
| PACAla = | picolinoyl ACAla |
| 3-Pal = | 3-(3-pyridyl) alanine |
| pClPhe = | 3-(4-chloro) phenylalanine |
| PicLys = | $N^E$-picolinoyllysine |
| Pro = | proline |
| PzACAla = | 3(4-pyrazinylcarbonylaminocyclohexyl) alanine |
| PzcLys = | $N^E$-pyrazinylcarbonyllysine |
| Ser = | serine |
| Tyr = | tyrosine |

In practicing the treatment method of the present invention the GnRH antagonist should be administered in an amount and frequency effective to substantially suppress endogenous gonadotropin levels during the treatment period. These parameters can be readily determined by the skilled practitioner and must obviously be adjusted to reflect the activity of the particular antagonist utilized and the needs of the particular patient being treated so as to optimize the results to be obtained.

Generally speaking, antagonists such as Antide are administered in amounts between about 0.001 and 10 mg/kg body weight per day, preferably about 0.1 to 3 mg/kg/day. It may be administered at the higher range of dose levels over a period of about one to six days to achieve a long term gonadotropin suppression lasting about four to eight weeks, at which point it can be readministered. Alternatively, it may be administered at the lower range of dose levels when it is administered more frequently such as daily, every other day, or weekly. It is preferred to administer the antagonist at regular intervals during the treatment period to maintain inhibition of gonadotropin secretion. This may be daily, every other day, weekly, biweekly or monthly depending on the dose and formulation. When the antagonist is administered over an initial loading period of several days, it is preferred to administer it once per day, or as a depot implant lasting several days per treatment. Of course, it is also possible, and may be desirable in some instances, to administer the antagonist in slow release form.

Upon administration of an effective amount of GnRH antagonist to suppress endogenous gonadotropin levels, gonadotropin releasing hormone (GnRH) is administered in an amount and frequency effective to induce secretion of gonadotropins to maintain a desired level. This desired level of gonadotropin secretion may be adjusted so as to induce ovulation if that is the intended goal.

The GnRH administration may be commenced after the first day of the GnRH antagonist administration, and preferably after completion of the GnRH antagonist administration where such administration comprises a high loading dose of antagonist administered over a short (1-6 day) period. In certain instances it may be desirable or preferred to commence GnRH administration during the period of antagonist administration (e.g. where the antagonist is administered throughout the treatment period) and, in fact, administration of both agents can commence at the same time and continue throughout the treatment period.

The amount of GnRH to be administered and the frequency of administration will obviously depend on the needs and condition of the patient being treated and the gonadotropin levels which are desired to be maintained in that patient. Typically, GnRH replacement therapy will continue daily during the treatment period, preferably in an episodic or pulsatile manner, generally at levels of about 5 to 10 μg/pulse every 60 to 120 minutes, preferably through an infusion pump. Where it is desired to induce ovulation in humans, the GnRH replacement therapy will ordinarily continue for about sixteen days, preferably followed by human chorionic gonadotropin.

The treatment method of the present invention is useful for controlling gonadotropin levels in mammals, particularly women, so that they can be maintained at a desired level, particularly levels within the normal range, and most particularly levels which will induce ovulation. This method is especially suitable for treating mammals, particularly women, with polycystic ovarian disease, hyperandrogenism, or abnormally high levels of luteinizing hormone.

For use in practicing the above-described method, this invention also contemplates a treatment kit which comprises a GnRH antagonist, as previously described, in a dosage form and quantity suitable for administering an amount and frequency effective to substantially suppress endogenous gonadotropin levels in the mammal to be treated, and GnRH in a dosage form and quantity suitable for administering an amount and frequency effective to induce secretion of gonadotropins in the mammal to be treated so as to maintain a desired gonadotropin level therein.

The GnRH antagonist may be formulated with any suitable pharmaceutically acceptable carrier and may be administered by any of a variety of routes including parenterally (including subcutaneous, intramuscular or intravenous administration), vaginally, rectally, buccally (including sublingually), transdermally or intranasally.

Pharmaceutical compositions may be prepared for use for parenteral (subcutaneous, intramuscular or intravenous) administration particularly in the form of liquid solutions or suspensions; for vaginal or rectal administration particularly in semisolid forms such as creams and suppositories; for oral or buccal administration particularly in the form of tablets or capsules; or for intranasal administration particularly in the form of powders, nasal drops or aerosols. Various slow release, depot implant or injectable dosage forms may also be utilized.

These compositions may conveniently be administered in unit dosage form and may be prepared by any of the methods well-known in the pharmaceutical art. Formulations for parenteral administration may contain as common excipients sterile water or saline, alkylene glycols such as propylene glycol, polyalklene glycols such as polyethylene glycol, oils of vegetable origin, hydrogenated naphthalenes and the like. Formulations for vaginal or rectal administration, e.g. suppositories, may contain as excipients, for example, polyalklenegylcols, vaseline, cocoa butter and the like. Formulations for nasal administration may be solid and contain as excipients, for example, lactose or dextran, or may be aqueous or oily solutions for administration in the form of nasal drops or metered spray. For buccal administration, typical excipients include sugars, calcium stearate, pregelatinated starch and the like. One or more surfactant acids or salts can be added to the solution or powder formulation. Suitable pharmaceutically acceptable surfactant salts will be those which retain the phenomenon of enhanced peptide absorption, as well as the compound's surfactant characteristics and which are not deleterious to the subject or otherwise contraindicated.

EXAMPLE 1

In order to demonstrate the continued long-term inhibition for endogenous gonadotropin secretion induced by GnRH antagonists and the response to GnRH replacement therapy, the following experiment was conducted.

Three long-term ovariectomized cynomolgus monkeys fitted with indwelling jugular vein canulae were utilized for this study. Daily blood samples were drawn under ketamine-induced anesthesia (10 mg/kg, I.M.), for 90 days. On study days 11–16 Antide (3 mg/kg, in propylene/glycol:water, 1:1) was administered via subcutaneous injection. GnRH replacement therapy (5 $\mu$g/pulse, 1 pulse/hour given over 1 min, via a Pulsamat infusion pump) was initiated on day 17 and continued for one week then withheld for one week, then reinitiated for one week in a 7 day on, 7 day off regimen for a total of four exposures.

The results of this experiment are depicted in FIG. 1 (LH only). A clear and profound inhibition of gonadotropin concentrations from pretreatment values of 200–300 ng/ml (LH) and 100–150 ng/ml (FSH) to less than 50 ng/ml occurred within 24 hours (LH) and 48 hours (FSH) of Antide administration. Gonadotropin concentrations remained fully suppressed until the day after initiation of GnRH replacement therapy when they returned to levels approximately characteristic of the ovariectomized animal (greater than 100 ng/ml). Upon cessation of GnRH replacement therapy gonadotropin concentrations again returned to a fully suppressed condition only to become re-elevated upon reinitiation of GnRH replacement therapy. Each time GnRH replacement therapy was initiated gonadotropin concentrations rose into the normal range, and each time GnRH replacement therapy was withheld gonadotropin concentrations fell to suppressed levels, thus revealing a square wave pattern or gonadotropin secretion synchronized to the delivery of GnRH. Eventual recovery to pretreatment conditions occurred at approximately 80 days, which is typical for recovery from Antide induced gonadotropin suppression under the six day dose regimen.

This study revealed two important observations: (1) The GnRH antagonist (specifically Antide) maintains its ability to suppress endogenous gonadotropin levels for an extended time interval; and (2) this inhibition of gonadotropin secretion can be overcome with an appropriate GnRH replacement therapy. It follows that gonadotropin levels can be carefully controlled and maintained at a desired level by adjusting the amount and frequency of the GnRH antagonist and GnRH in a manner suitable to achieve that level in the mammal being treated.

EXAMPLE 2

A second experiment was performed to establish that pulsatile GnRH replacement therapy would induce ovulation in the face of antagonist-induced suppression of endogenous cycles.

Normally cycling cynomolgus monkeys were studied in one of two regimens. Regimen A comprised a series of initial large loading doses of Antide (10 mg/kg, sc), with no further Antide administration. Regimen B comprised an initial 3 mg/kg loading dose followed by 1 mg/kg administered every other day to sustain Antide concentrations at a constant level until ovulation had been successfully induced. In each regimen GnRH replacement was initiated 4 days after the first Antide injection at a rate of 5 $\mu$g/pulse, with one 1 min pulse/hour. The amplitude was subsequently raised to 10 $\mu$g/pulse after approximately 21 days. Daily blood samples were drawn for later determination of estradiol, progesterone and Antide concentrations.

In the monkey treated via regimen A, Antide was administered during the luteal phase as four daily injections of 10 mg/kg. As expected, the concentration of Antide rose rapidly to very high levels (>300 ng/ml) then declined throughout the test period (>40 days), always remaining above 15 ng/ml. The initial pulsatile GnRH replacement (5 $\mu$g/pulse) resulted in the elevation of $E_2$ (estradiol) concentrations to those characteristic of the late follicular phase (100 to 200 pg/ml). However, a pump failure on study day 32 resulted in the loss of that cohort of follicles. When the GnRH pump was restarted, the amplitude of the GnRH pulses was increased to 10 $\mu$g/pulse. This resulted in a rapid and sustained elevation of $E_2$ concentrations culminating in ovulation and normal luteal phase $P_4$ (progesterone) concentrations.

In the monkey treated via regimen B, Antide was administered as an initial 3 mg/kg bolus followed by 1 mg/kg every other day to achieve a sustained elevation of Antide until ovulation had been successfully achieved. Concentrations of Antide rose promptly to levels between 10 and 20 ng/ml where they remained throughout the course of the study. Once again the initial pulsatile GnRH replacement resulted in elevations of $E_2$ to those characteristic of the late follicular phase. However, once again therapy had to be discontinued, this time due to a minor infection at the site of needle insertion from the pump. Upon re-initiation of therapy (5 $\mu$g/pulse) $E_2$ concentrations again rose slowly, but seemed to plateau at 50 to 70 pg/ml. The GnRH pulse amplitude was increased to 10 $\mu$g/pulse, which resulted in a rapid rise in $E_2$ concentrations to normal preovulatory levels culminating in ovulation with subsequent normal luteal $P_4$ production.

From these studies it is evident that pulsatile GnRH replacement therapy can be used to induce ovulation in mammals which are treated with GnRH antagonists to reduce endogenous gonadotropin levels.

What is claimed is:

1. A method of controlling gonadotropin levels in a mammal for a defined treatment period which comprises administering a gonadotropin releasing hormone (GnRH) antagonist in an amount and frequency effective to substantially suppress endogenous gonadotropin levels in said mammal throughout the treatment period and administering gonadotropin releasing hormone (GnRH) in an amount and frequency effective to induce secretion of gonadotropins to maintain a desired level in said mammal throughout the treatment period.

2. A method of inducing ovulation in a mammal which comprises administering a GnRH antagonist in an amount and frequency effective to substantially suppress endogenous gonadotropin levels and administering GnRH in an amount and frequency effective to induce ovulation.

3. A method according to claim 1 or 2 wherein said mammal has polycystic ovarian disease.

4. A method according to claim 1 or 2 wherein said mammal has hyperandrogenism.

5. A method according to claim 1 wherein said mammal has abnormally high levels of luteinizing hormone which are reduced to approximately normal levels as a result of treatment.

6. A method according to claim 1 or 2 wherein said GnRH antagonist comprises a decapeptide of the formula

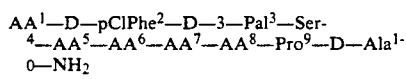

wherein
AA$^1$ is N—Ac—D—2—Nal, N—Ac—D—pClPhe or N—Ac—D—Cl$_2$Phe;
AA$^5$ is Tyr, acylated Lys, or acylated ACAla;
AA$^6$ is D-acylated Lys or D-acylated ACAla;
AA$^7$ is Leu, Aile, Nle, Val, NVal, Abu, or Ala; and
AA$^8$ is ILys or IOrn.

7. A method according to claim 6 wherein
AA$^1$ is N-Ac-D-2-Nal
AA$^5$ is NicLys, PicLys, MNicLys, MPicLys, INicLys, DMGLys, or PzcLys; and
AA$^6$ is D-NicLys, D-PicLys, D-MNicLys, D-MPicLys, D-INicLys, D-BzLys, D-PzcLys, D-PzACAla, D-NACAla, or D-PACAla.

8. A method according to claim 6 wherein said GnRH antagonist is Antide.

9. A method according to claim 1 wherein said GnRH antagonist is initially administered over a period of one to six days.

10. A method according to claim 1 wherein said GnRH antagonist is administered at approximately regular intervals.

11. A method according to claim 10 wherein said GnRH antagonist is administered daily, every other day, weekly, bi-weekly or monthly.

12. A method according to claim 9 wherein said GnRH antagonist is administered approximately monthly.

13. A method according to claim 9 wherein GnRH administration commences after the first day of GnRH antagonist administration.

14. A method according to claim 9 wherein GnRH administration commences after completion of GnRH antagonist administration.

15. A method according to claim 1 or 2 wherein said GnRH is administered in an episodic or pulsatile manner.

16. A method according to claim 15 wherein said GnRH is administered at about 5 to 10 μg/pulse at about 60 to 120 minute intervals.

17. A method according to claim 6 wherein said GnRH is administered in a pulsatile manner at about 5 to 10 μg/pulse at about 60 to 120 minute intervals.

18. A method according to claim 17 wherein said GnRH antagonist is Antide.

* * * * *